(12) United States Patent
Tanzer

(10) Patent No.: US 6,680,423 B1
(45) Date of Patent: Jan. 20, 2004

(54) ABSORBENT ARTICLE HAVING REINFORCED ELASTIC ABSORBENT CORE

(75) Inventor: Richard Warren Tanzer, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/385,141

(22) Filed: Aug. 27, 1999

(51) Int. Cl.⁷ .......................... A61F 13/15; A61F 13/20
(52) U.S. Cl. ...................................... 604/380; 604/367
(58) Field of Search ........................... 442/328, 329, 442/381, 409, 417; 604/380, 378, 379, 383, 385.1

(56) References Cited

U.S. PATENT DOCUMENTS

| | | | |
|---|---|---|---|
| 3,338,992 A | 8/1967 | Kinney | 264/24 |
| 3,341,394 A | 9/1967 | Kinney | 161/72 |
| 3,485,706 A | 12/1969 | Evans | 161/72 |
| 3,502,538 A | 3/1970 | Peterson | 161/150 |
| 3,502,763 A | 3/1970 | Hartmann | 264/210 |
| 3,542,615 A | 11/1970 | Dobo | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 3,901,236 A | 8/1975 | Assarsson et al. | 128/284 |
| 4,076,663 A | 2/1978 | Masuda et al. | 260/17.4 GC |
| 4,100,324 A | 7/1978 | Anderson et al. | 428/288 |
| 4,259,387 A | 3/1981 | Mesek | 428/167 |
| 4,286,082 A | 8/1981 | Tsubakimoto et al. | 526/240 |
| 4,340,563 A | 7/1982 | Appel et al. | 264/518 |
| 4,421,812 A * | 12/1983 | Plant | 428/152 |
| 4,422,892 A * | 12/1983 | Plant | 156/209 |
| 4,720,415 A * | 1/1988 | Vander Wielen et al. | 428/152 |
| 4,818,464 A | 4/1989 | Lau | 264/510 |
| 4,847,134 A | 7/1989 | Fahrenkrug et al. | 428/138 |
| 5,332,613 A * | 7/1994 | Taylor et al. | 428/152 |
| 5,364,382 A | 11/1994 | Latimer et al. | 604/378 |
| 5,366,452 A | 11/1994 | Widlund et al. | 604/385.2 |
| 5,376,198 A | 12/1994 | Fahrenkrug et al. | 156/164 |
| 5,385,775 A * | 1/1995 | Wright | 428/284 |
| 5,389,095 A | 2/1995 | Suzuki et al. | 604/385.2 |
| 5,409,768 A * | 4/1995 | Dickenson et al. | 428/283 |
| 5,411,497 A | 5/1995 | Tanzer et al. | 604/368 |
| 5,425,725 A | 6/1995 | Tanzer et al. | 604/368 |
| 5,433,715 A | 7/1995 | Tanzer et al. | 604/368 |
| 5,451,219 A | 9/1995 | Suzuki et al. | 604/385.2 |
| 5,509,915 A | 4/1996 | Hanson et al. | 604/378 |
| 5,516,569 A * | 5/1996 | Veith et al. | 428/68 |

(List continued on next page.)

FOREIGN PATENT DOCUMENTS

WO      96/16624      6/1996      ........... A61F/13/15

OTHER PUBLICATIONS

*Cellular Materials to Composites*, Encyclopedia of Polymer Science and Engineering, vol. 3, John Wiley & Sons, pp. 299–300 (1985).

*Primary Examiner*—Weilun Lo
*Assistant Examiner*—Michele Kidwell
(74) *Attorney, Agent, or Firm*—Pauley Peterson & Erickson

(57) ABSTRACT

An absorbent elastic nonwoven composite material having stretch properties in a machine direction includes an elastic filament matrix and, contained with the matrix, absorbent fibers and a superabsorbent material. A plurality of bond lines oriented in a direction transverse to the machine direction provides reinforcement of the elastic filament matrix so that, when the composite material is stretched, there is less tearing and separation of the elastic filaments. The reinforcement by the bonding lines reduces the separation and shake-out of the absorbent and superabsorbent materials from the matrix during stretching and recovery of the composite material, and improves the recovery. The absorbent elastic nonwoven composite material is useful in a wide variety of personal care absorbent articles and medical absorbent articles.

32 Claims, 2 Drawing Sheets

U.S. PATENT DOCUMENTS

| | | | |
|---|---|---|---|
| 5,520,673 A | 5/1996 | Yarbrough et al. | 604/378 |
| 5,560,878 A | 10/1996 | Dragoo et al. | 264/115 |
| 5,591,155 A * | 1/1997 | Nishikawa et al. | 604/393 |
| 5,593,399 A | 1/1997 | Tanzer et al. | 604/368 |
| 5,601,542 A | 2/1997 | Melius et al. | 604/368 |
| 5,614,281 A * | 3/1997 | Jackson et al. | 428/100 |
| 5,645,542 A | 7/1997 | Anjur et al. | 604/368 |
| 5,662,634 A | 9/1997 | Yamamoto et al. | 604/378 |
| 5,683,374 A | 11/1997 | Yamamoto et al. | 604/385.2 |
| 5,722,967 A * | 3/1998 | Coles | 604/385.1 |
| 5,803,077 A * | 9/1998 | Gazzara | 128/205.27 |
| 5,807,365 A * | 9/1998 | Luceri | 604/367 |
| 5,824,004 A | 10/1998 | Osborn, III et al. | 604/385.2 |
| 5,883,028 A | 3/1999 | Morman et al. | 442/394 |
| 5,993,431 A * | 11/1999 | McFall et al. | 604/385.2 |

* cited by examiner

ABSORBENT ARTICLE HAVING REINFORCED ELASTIC ABSORBENT CORE

FIELD OF THE INVENTION

This invention is directed to an absorbent article having an elastic absorbent core. The absorbent core is reinforced and strong thereof using high density bonding lines which extend transverse to the direction of stretching.

BACKGROUND OF THE INVENTION

There is a trend in the absorbent garment industry to make absorbent articles, such as diapers, more stretchable. In the past, these absorbent articles have been made primarily from inelastic materials. Limited stretchability was accomplished by incorporating elastic bands in the waist and/or leg regions of the garments. More recently, there have been attempts to make these articles elastic throughout.

Absorbent articles contain multiple layers. Disposable diapers, for instance, typically contain a liquid permeable body-side liner, a substantially liquid impermeable outer cover, an absorbent core layer between the body-side liner and the outer cover and, often, a surge management layer on either side of the body-side liner which properly channels a liquid insult toward the absorbent core. To make an absorbent article completely elastic requires that all of the layers be stretchable or extensible, and that at least one of the layers be elastically recoverable. If even one of the layers cannot be stretched, then the entire article cannot be stretched.

Various technologies are known for making the body-side liner and outer cover elastic or stretchable. However, making the absorbent core elastic or stretchable poses a greater challenge. Absorbent core layers often contain a high weight percentage of one or more absorbent media such as wood pulp fibers, fluff, superabsorbent particles or fibers, or the like, entangled and dispersed in a lower weight percentage of a fibrous matrix material. Stretching of the absorbent core can cause tearing of the relatively sparse fibrous matrix, and/or shake-out of the absorbent and superabsorbent materials. There is a need for desire for a stretchable absorbent composite which is able to withstand stretching and retraction with minimal tearing and shake-out.

SUMMARY OF THE INVENTION

The present invention is directed to a conformable, comfortable and highly absorbent elastic nonwoven composite which addresses the foregoing concerns.

The absorbent nonwoven composite includes a mixture of nonwoven elastomeric polymer fibers, absorbent fibers, and superabsorbent particles or fibers. The elastomeric polymer fibers may be substantially continuous or staple in length, and preferably are substantially continuous. In one embodiment, the nonwoven elastic polymer fibers constitute less than 20% by weight of the absorbent nonwoven composite, and at least about 3% by weight of the absorbent nonwoven composite. The absorbent fibers and superabsorbent particles or fibers each constitute about 20–77% by weight of the absorbent nonwoven composite. Composites of this general nature are described in U.S. patent application Ser. No. 09/197,268 filed Nov. 20, 1998 in the name of McDowall et al., which is incorporated by reference.

In another embodiment, having higher integrity but somewhat less absorbency, the nonwoven elastomeric polymer fibers constitute about 20–80% by weight of the absorbent nonwoven composite. The absorbent fibers and superabsorbent particles or fibers each constitute about 10–70% by weight of the absorbent nonwoven composite. Composites of this general nature are disclosed in U.S. Pat. No. 5,645,542, issued to Anjur et al., which is incorporated by reference.

The absorbent nonwoven composites are elastic in at least a machine direction. The "machine direction" is the direction of primary orientation of the elastomeric polymer fibers that form the matrix for containing the absorbent and superabsorbent materials. The machine direction corresponds to the direction of movement of a conveying belt or similar apparatus used during extrusion of the elastomeric polymer fibers and combination of the elastomeric polymer fibers with the absorbent and superabsorbent ingredients. When the elastomeric polymer fibers are substantially continuous, one way to determine the machine direction in an absorbent nonwoven composite is to draw a 5 cm×5 cm square on a sample of the composite. Most of the elastic polymer filaments will pass through two of the four sides of the square, thereby defining the machine direction.

In accordance with the invention, the absorbent composite is reinforced by forming a plurality of bond lines transverse to the machine direction. The bond lines can be formed using one or more of ultrasonic bonding, thermal bonding, pressure bonding, and adhesive bonding techniques. Preferably, the bonding creates densified regions along the bond lines.

The bond lines provide the absorbent composite with increased strength and recovery during stretching, and somewhat less extensibility. The increased strength results from stabilization of the elastic polymer fibers, which are anchored or locked into place at the densified, bonded regions. This anchoring at periodic intervals alleviates tearing of the elastic polymer matrix fibers during stretching. The reduced tearing also results in improved elastic recovery of the absorbent composite. Furthermore, the stabilization of the elastic polymer matrix fibers at periodic intervals restricts lateral separation of the fibers, thereby reducing shake-out of the absorbent and superabsorbent material.

With the foregoing in mind, it is a feature and advantage of the invention to provide a reinforced elastic absorbent composite having improved strength and recovery, for use in absorbent articles.

It is also a feature and advantage of the invention to provide a personal care absorbent article with elastic properties, using the elastic absorbent composite of the invention.

It is also a feature and advantage of the invention to provide a medical absorbent article having elastic properties, using the elastic absorbent composite of the invention.

These and other features and advantages will become further apparent from the following detailed description of the presently preferred embodiments, read with the accompanying drawings.

DEFINITIONS

Figure 1:
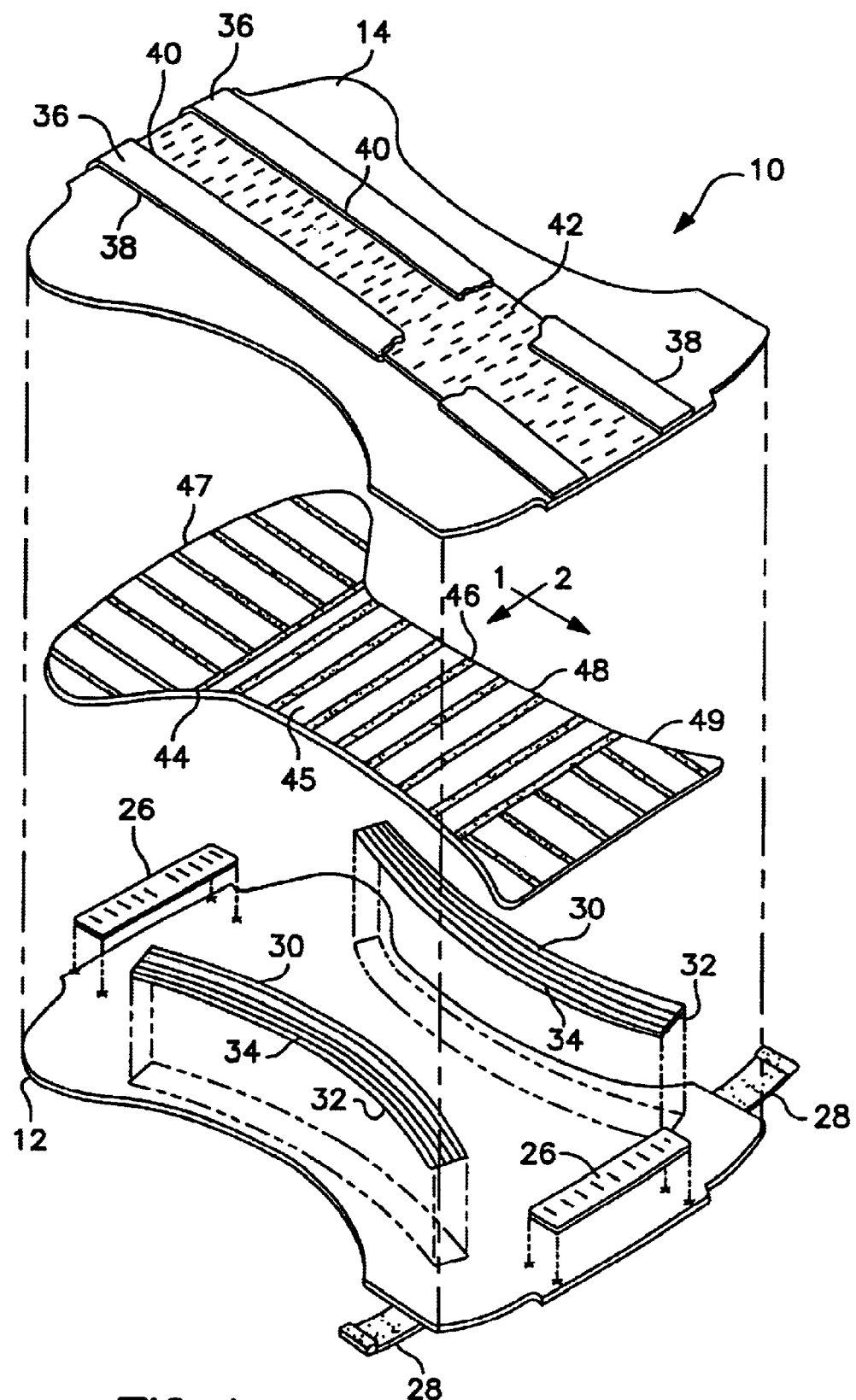
FIG. 1 is an exploded perspective view of an absorbent article according to the invention, in this case, a diaper.

The term "nonwoven fabric or web" means a web having a structure of individual fibers or filaments which are interlaid, but not in an identifiable manner as in a knitted fabric. The terms "fiber" and "filament" are used herein interchangeably. Nonwoven fabrics or webs have been formed from many processes such as, for example, meltblowing processes, spunbonding processes, air laying processes, and bonded carded web processes. The term also includes films that have been perforated or otherwise treated to allow air to pass through. The basis weight of nonwoven fabrics is usually expressed in ounces of material per square yard (osy) or grams per square meter (gsm) and the fiber diameters are usually expressed in microns. (Note that to convert from osy to gsm, multiply osy by 33.91.)

The term "microfibers" means small diameter fibers having an average diameter not greater than about 75 microns, for example, having an average diameter of from about 1 micron to about 50 microns, or more particularly, having an average diameter of from about 1 micron to about 30 microns.

The term "spunbonded fibers" refers to small diameter fibers which are formed by extruding molten thermoplastic material as filaments from a plurality of fine capillaries of a spinnerette having a circular or other configuration, with the diameter of the extruded filaments then being rapidly reduced by air impingement as explained, for example, in U.S. Pat. No. 4,340,563 to Appel et al., U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,502,538 to Petersen, and U.S. Pat. No. 3,542,615 to Dobo et al. Spunbond fibers are quenched and generally not tacky on the surface when they enter the draw unit, or when they are deposited onto a collecting surface. Spunbond fibers are generally continuous and may have average diameters larger than 7 microns, often between about 10 and 30 microns.

The term "meltblown fibers" means fibers formed by extruding a molten thermoplastic material through a plurality of fine, usually circular, die capillaries as molten threads or filaments into converging high velocity heated gas (e.g., air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed for example, in U.S. Pat. No. 3,849,241 to Butin et al. Meltblown fibers are microfibers which may be continuous or discontinuous, are generally smaller than 10 microns in diameter, and are generally self bonding when deposited onto a collecting surface. Meltblown fibers used in the invention are preferably substantially continuous.

The term "substantially continuous filaments or fibers" refers to filaments or fibers prepared by extrusion from a spinnerette, including without limitation spunbonded and meltblown fibers, which are not cut from their original length prior to being formed into a nonwoven web or fabric. Substantially continuous filaments or fibers may have lengths ranging from greater than about 15 cm to more than one meter; and up to the length of the nonwoven web or fabric being formed. The definition of "substantially continuous filaments or fibers" includes those which are not cut prior to being formed into a nonwoven web or fabric, but which are later cut when the nonwoven web or fabric is cut.

The term "staple filaments or fibers" means filaments or fibers which are natural or which are cut from a manufactured filament prior to forming into a web, and which have a length ranging from about 0.1–15cm, more commonly about 0.2–7 cm.

The term "fiber" or "fibrous" is meant to refer to a particulate material wherein the length to diameter ratio of such particulate material is greater than about 10. Conversely, a "nonfiber" or "nonfibrous" material is meant to refer to a particulate material wherein the length to diameter ratio of such particulate material is about 10 or less.

The terms "elastic" and "elastomeric" are used interchangeably to mean a material that is generally capable of recovering its shape after deformation when the deforming force is removed. Specifically, as used herein, elastic or elastomeric is meant to be that property of any material which upon application of a biasing force, permits that material to be stretchable to a stretched biased length which is at least about 25 percent greater than its relaxed unbiased length, and that will cause the material to recover at least 40 percent of its elongation upon release of the stretching elongating force. A hypothetical example which would satisfy this definition of an elastomeric material would be a one (1) inch sample of a material which is elongatable to at least 1.25 inches and which, upon being elongated to 1.25 inches and released, will recover to a length of not more than 1.15 inches. Many elastic materials may be stretched by much more than 25 percent of their relaxed length, and many of these will recover to substantially their original relaxed length upon release of the stretching, elongating force. This latter class of materials is generally beneficial for purposes of the present invention.

The term "recover" or "retract" relates to a contraction of a stretched material upon termination of a biasing force following stretching of the material by application of the biasing force.

The term "superabsorbent material" refers to a water swellable, water-insoluble organic or inorganic material capable, under the most favorable conditions, of absorbing at least about 20 times its weight, preferably at least about 30 times its weight in an aqueous solution containing 0.9% by weight sodium chloride. The term "absorbent material" refers to a material which absorbs from about 1 to less than 20 times its weight in an aqueous solution containing 0.9% by weight sodium chloride. INDA Standard Test Method IST 10.1 (95), entitled "Standard Test Method for Absorbency Time, Absorbency Capacity, and Wicking Time," published by INDA, Association of the Nonwoven Fabrics Industry, Cary, N.C., provides the basis for a suitable test method to measure absorbency. The "Absorptive Capacity Test (for small specimens)" may be used to determine the absorbency of a material for the purpose of the subject invention with the following two modifications: (i) IST 10.1 (95) specifies that water is to be used; substitute a 0.9% aqueous sodium chloride solution, (ii) IST 10.1 (95) specifies that a 5 gram sample is used. If necessary, a smaller sample, obtained from an absorbent product may be used instead.

The term "pulp fibers" refers to fibers from natural sources such as woody and non-woody plants. Woody plants include, for example, deciduous and coniferous trees. Non-woody plants include, for instance, cotton, flax, esparto grass, milkweed, straw, jute hemp, and bagasse.

The term "absorbent article" includes without limitation diapers, training pants, swim wear, absorbent underpants, adult incontinence products, feminine hygiene products and medical absorbent products (for example, absorbent medical garments, underpads, bandages, drapes, and medical wipes).

The term "machine direction" refers to a direction of primary orientation of fibers in a thermoplastic nonwoven web. Following extrusion of nonwoven web filaments, such as spunbond or meltblown filaments, the filaments are typically cooled and carried away on a conveying device or similar apparatus. The machine direction is the direction of primary orientation assumed by the filaments in a nonwoven web, resulting from being drawn and carried away.

The term "transverse direction" refers both to directions perpendicular to the machine direction, and directions within plus or minus 45 degrees of perpendicular to the machine direction.

DETAILED DESCRIPTION OF THE PRESENTLY PREFERRED EMBODIMENTS

The present invention is directed to an elastic absorbent nonwoven web composite, and an absorbent article which utilizes it. One preferred absorbent article is a disposable diaper. FIG. 1 illustrates an exploded perspective view of a disposable diaper according to one preferred embodiment of the invention. Disposable diaper 10 includes an outer cover 12, a body-side liner 14, and an absorbent composite 44 located between the outer cover 12 and body-side liner 14.

Attached to outer cover 12 are waist elastics 26, fastening tapes 28 and leg elastics 30. The leg elastics 30 comprise a carrier sheet 32 and individual elastic strands 34.

The body-side liner 14 includes containment flaps 36 having proximal edges 38 and distal edges 40. A surge management layer 42 is located between the proximal edges 38 of the containment flaps 36.

A possible construction method and materials of a diaper similar to the one illustrated in FIG. 1 are set forth in greater detail in commonly assigned U.S. Pat. No. 5,509,915, issued Apr. 25, 1996 in the name of Hanson et al., incorporated herein by reference. Possible modifications to the diaper illustrated in FIG. 1 are set forth in commonly assigned U.S. Pat. No. 5,509,915 referenced above and in commonly assigned U.S. Pat. No. 5,364,382, issued Nov. 15, 1994 in the name of Latimer et al. Such possible modifications include positioning the surge management layer 42 between the body-side liner 14 and the absorbent composite 44 and reducing the length of the surge management layer to extend the length of the absorbent composite or massing (reduce length and increase basis weight) the surge management layer in the area of the diaper where liquid waste initially accumulates (target zone).

In one embodiment, an absorbent elastic nonwoven web composite having high loading of an absorbent material and excellent conformability is provided as the composite 44. In this embodiment, the absorbent elastic nonwoven web composite includes about 3 to less than 20 percent by weight of an elastic filament matrix including a plurality of thermoplastic elastomeric nonwoven filaments, about 20–77% by weight absorbent fibers, and about 20–77% by weight of a superabsorbent material. The absorbent fibers and superabsorbent material are contained in the matrix. Preferably, the absorbent elastic nonwoven web composite includes about 5–18% by weight of the elastic filament matrix about 25–70% by weight absorbent fibers, and about 25–70% by weight superabsorbent material. More preferably, the absorbent elastic nonwoven web composite includes about 5–15% by weight of the elastic filament matrix, about 30–62% by weight absorbent fibers, and about 40–65% by weight superabsorbent material.

In another embodiment, an absorbent elastic nonwoven web composite having somewhat greater strength and elastic recovery, yet somewhat less absorbency, is provided as the composite 44. In this second embodiment, the absorbent elastic nonwoven web composite includes about 20–80% by weight of the elastic filament matrix including thermoplastic elastomeric nonwoven filaments, about 10–70% by weight absorbent fibers, and about 10–70% by weight superabsorbent material. Again, the absorbent fibers and superabsorbent material are contained in the matrix. Preferably, the absorbent elastic nonwoven web composite includes about 25–60% of the elastic filament matrix, about 15–60% by weight of the absorbent fibers and about 15–60% by weight of the superabsorbent material.

Materials suitable for use in preparing the thermoplastic elastomeric fibers herein include diblock, triblock, or multiblock elastomeric copolymers such as olefinic copolymers, including styrene-isoprene-styrene, styrene-butadiene-styrene, styrene-ethylenebutylene-styrene, or styrene-ethylene/propylene-styrene, which may be obtained from the Shell Chemical Company, under the trade designation KRATON® elastomeric resin; polyurethanes, including those available from E. I. Du Pont de Nemours Co., under the trade name LYCRA® polyurethane; polyamides, including polyether block amides available from Ato Chemical Company, under the trade name PEBAX® polyether block amide; polyesters, such as those available from E. I. Du Pont de Nemours Co., under the trade name HYTREL® polyester; and single-site or metallocene-catalyzed polyolefins having density less than about 0.89 grams/cc, available from Dow Chemical Co. under the trade name AFFINITY®, and from Exxon Chemical Co. under the trade name EXACT®.

A number of block copolymers can be used to prepare the thermoplastic elastomeric fibers useful in this invention. Such block copolymers generally comprise an elastomeric midblock portion B and a thermoplastic endblock portion A. The block copolymers used in this invention generally have a three-dimensional physical crosslinked structure below the endblock portion glass transition temperature and are elastomeric. The block copolymers are also thermoplastic in the sense that they can be melted, formed, and resolidified several times with little or no change in physical properties (assuming a minimum of oxidative degradation).

Endblock portion A generally comprises a poly (vinylarene), such as polystyrene, having an average molecular weight between 1,000 and 60,000. Midblock portion B generally comprises a substantially amorphous polyolefin such as polyisoprene, ethylene/propylene polymers, ethylene/butylene polymers, polybutadiene, and the like, or mixtures thereof, having an average molecular weight between about 5,000 and about 450,000. The total molecular weight of the block copolymer is suitably about 10,000 to about 500,000 and more suitably about 200,000 to about 300,000.

Some suitable block copolymers used in this invention comprise at least two substantially polystyrene endblock portions and at least one substantially ethylene/butylene mid-block portion. As an example, ethylene/butylene typically may comprise the major amount of the repeating units in such a block copolymer and can constitute, for example, 70 percent by weight or more of the block copolymer. The block copolymer can have three or more arms, and good results can be obtained with, for example, four, five, or six arms. The midblock portion can be hydrogenated, if desired.

Linear block copolymers, such as A-B-A, A-B-A-B-A or the like, are suitably selected on the basis of endblock content, large endblocks being preferred. For polystyrene-ethylene/butylene-polystyrene block copolymers, a styrene content in excess of about 10 weight percent is suitable, such as between about 12 to about 30 weight percent. With higher styrene content, the polystyrene endblock portions generally have a relatively high molecular weight. A commercially available example of such a linear block copolymer is a styrene-ethylene/butylene-styrene block copolymer which contains about 13 weight percent styrene units and essentially the balance being ethylene/butylene units, commercially available from the Shell Chemical Company, under the trade designation KRATON® G1657 elastomeric resin. Typical properties of KRATON® G1657 elastomeric resin are reported to include a tensile strength of 3400 pounds per square inch ($2.3 \times 10^7$ Pascals), a 300 percent modulus of 350 pounds per square inch ($2.4 \times 10^6$ Pascals), an elongation of 750 percent at break, a Shore A hardness of 65, and a Brookfield viscosity, when at a concentration of 25 weight percent in a toluene solution, of about 4200 centipoise at room temperature. Another suitable elastomer, KRATON® G2740, is a styrene butadiene block copolymer blended with tackifier and low density polyethylene.

Other suitable elastomeric polymers may also be used to make the thermoplastic elastic fibers. These include, without limitation, elastomeric (single-site or metallocene catalyzed) polypropylene, polyethylene and other alpha-olefin homopolymers and copolymers, having density less than about 0.89 grams/cc; ethylene vinyl acetate copolymers; and substantially amorphous copolymers and terpolymers of ethylene-propylene, butene-propylene, and ethylene-propylene-butene.

Metallocene-catalyzed elastomeric polymers are relatively new, and are presently preferred. The metallocene process for making polyolefins uses a metallocene catalyst which is activated (i.e., ionized) by a co-catalyst.

Polymers produced using metallocene catalysts have a narrow molecular weight distribution. "Narrow molecular weight distribution polymer" refers to a polymer that exhibits a molecular weight distribution of less than about 3.5. As is known in the art, the molecular weight distribution of a polymer is the ratio of the weight average molecular weight of the polymer to the number average molecular weight of the polymer. Methods of determining molecular weight distribution are described in the *Encyclopedia of Polymer Science and Engineering*, Volume 3, Pages 299–300 (1985). Examples of narrow molecular weight distribution polyolefins include the metallocene-catalyzed polyolefins, the single-site catalyzed polyolefins, and the constrained geometry-catalyzed polyolefins described above. As is known in the art, the metallocene-catalyzed polyolefins and the constrained geometry-catalyzed polyolefins are sometimes referred to as types of single-site catalyzed polymers. Polydispersities ($M_w/M_n$) of below 3.5 and as even below 2 are possible for metallocene produced polymers. These polymers also have a narrow short chain branching distribution when compared to otherwise similar Ziegler-Natta produced polymers.

The elastomeric fibers may be substantially continuous or staple in length, but are preferably substantially continuous. Substantially continuous filaments exhibit better containment of the cellulose fibers and superabsorbent material, have better elastic recovery and provide better distribution of liquids, than staple length fibers. The elastomeric fibers may be produced using a spunbonding process, a meltblowing process, or another suitable process. The elastomeric fibers may have an average diameter of about 1–75 microns, preferably about 1–40 microns, more preferably about 1–30 microns.

The absorbent fibers used in composite 44 may be any liquid-absorbing natural or synthetic fibers which are capable, under the most favorable conditions, of absorbing about 1 to less than 20 times their weight in an aqueous solution containing 0.9% by weight sodium chloride. Absorbent fibers include without limitation rayon staple fibers, cotton fibers, natural cellulose fibers such as wood pulp fibers and cotton linters, other pulp fibers, and fiberized feathers (e.g., fiberized poultry feathers, such as fiberized chicken feathers.)

Pulp fibers are especially useful as the absorbent fibers in the elastomeric nonwoven web composite. Preferred pulp fibers include cellulose pulp fibers, and the like. Other types of absorbent pulp may also be employed.

The pulp fibers may be unrefined or may be beaten to various degrees of refinement. Crosslinking agents and/or hydrating agents may also be added to the pulp mixture. Debonding agents may be added to reduce the degree of hydrogen bonding if a very open or loose nonwoven pulp fiber web is desired. One exemplary debonding agent is available from the Quaker Oats Chemical Company, Conshohocken, Pennsylvania, under the trade designation Quaker 2008. The addition of certain debonding agents in the amount of, for example, 1–4% by weight of the composite, may reduce the measured static and dynamic coefficients of friction and improve the abrasion resistance of the thermoplastic continuous polymer filaments. The debonding agents act as lubricants or friction reducers. Debonded pulp fibers are commercially available from Weyerhaeuser Corp. under the designation NB405.

The superabsorbent material used in composite 44 may be in the form of fibers, particles, or combinations thereof. As explained above, the term "superabsorbent" or "superabsorbent material" refers to a water-swellable, water-insoluble organic or inorganic material capable, under the most favorable conditions, of absorbing at least about 20 times its weight and, more desirably, at least about 30 times its weight in an aqueous solution containing 0.9 weight percent sodium chloride.

The superabsorbent materials can be natural, synthetic and modified natural polymers and materials. In addition, the superabsorbent materials can be inorganic materials, such as silica gels, or organic compounds such as cross-linked polymers. The term "cross-linked" refers to any means for effectively rendering normally water-soluble materials substantially water insoluble but swellable. Such means can include, for example, physical entanglement, crystalline domains, covalent bonds, ionic complexes and associations, hydrophilic associations, such as hydrogen bonding, and hydrophobic associations or Van der Waals forces.

Examples of synthetic superabsorbent material polymers include the alkali metal and ammonium salts of poly(acrylic acid) and poly(methacrylic acid), poly(acrylamides), poly (vinyl ethers), maleic anhydride copolymers with vinyl ethers and alpha-olefins, poly(vinyl pyrrolidone), poly (vinylmorpholinone), poly(vinyl alcohol), and mixtures and copolymers thereof. Further superabsorbent materials include natural and modified natural polymers, such as hydrolyzed acrylonitrilegrafted starch, acrylic acid grafted starch, methyl cellulose, chitosan, carboxymethyl cellulose, hydroxypropyl cellulose, and the natural gums, such as alginates, xanthan gum, locust bean gum and the like. Mixtures of natural and wholly or partially synthetic superabsorbent polymers can also be useful in the present invention. Other suitable absorbent gelling materials are disclosed by Assarsson et al. in U.S. Pat. No. 3,901,236 issued Aug. 26, 1975. Processes for preparing synthetic absorbent gelling polymers are disclosed in U.S. Pat. No. 4,076,663 issued Feb. 28, 1978 to Masuda et al. and U.S. Pat. No. 4,286,082 issued Aug. 25, 1981 to Tsubakimoto et al.

Superabsorbent materials may be xerogels which form hydrogels when wetted. The term "hydrogel," however, has commonly been used to also refer to both the wetted and unwetted forms of the superabsorbent polymer material. The superabsorbent materials can be in many forms such as flakes, powders, particulates, fibers, continuous fibers, networks, solution spun filaments and webs. The particles can be of any desired shape, for example, spiral or semi-spiral, cubic, rod-like, polyhedral, etc. Needles, flakes, fibers, and combinations may also be used.

Superabsorbents are generally available in particle sizes ranging from about 20 to about 1000 microns. Examples of suitable commercially available particulate superabsorbents include SANWET® IM 3900 and SANWET® IM-5000P, available from Hoescht Celanese located in Portsmouth, Va., DRYTECH® 2035LD available from Dow Chemical Co. located in Midland, Mich., and FAVOR® SXM 880, available from Stockhausen located in Greensboro, N.C. An example of a fibrous superabsorbent is OASIS® 101, available from Technical Absorbents, located in Grimsby, United Kingdom.

The thermoplastic elastomeric nonwoven filaments may be combined with the absorbent and superabsorbent materials using processes well known in the art. For example, a coform process may be employed, in which at least one meltblown diehead is arranged near a chute through which other materials are added while the web is forming. Coform processes are described in U.S. Pat. No. 4,818,464 to Lau and U.S. Pat. No. 4,100,324 to Anderson et al., the disclosures of which are incorporated by reference. The thermoplastic elastomeric filaments and absorbent and superabsorbent material may also be combined using hydraulic entangling or mechanical entangling. A hydraulic entangling process is described in U.S. Pat. No. 3,485,706 to Evans, the disclosure of which is incorporated by reference. After combining the ingredients, the absorbent elastic nonwoven composite may be bonded together using the through-air bonding or thermal point bonding techniques described above, to provide a coherent high integrity structure.

Alternatively, the absorbent structures can be formed as layered structures using two die tips to extrude the elastomeric filaments, and injecting the absorbent and superabsorbent materials as a middle layer between two elastomeric filament layers. Various degrees of mixing of elastomeric filaments and the absorbent/superabsorbent materials can be accomplished to facilitate regions of greater and lesser concentration of elastomeric filaments. This layered structure is an alternative to the absorbent structures produced by a coform process, in which the absorbent ingredients are substantially evenly distributed among individual filaments of an elastomeric nonwoven web.

Figure 2:
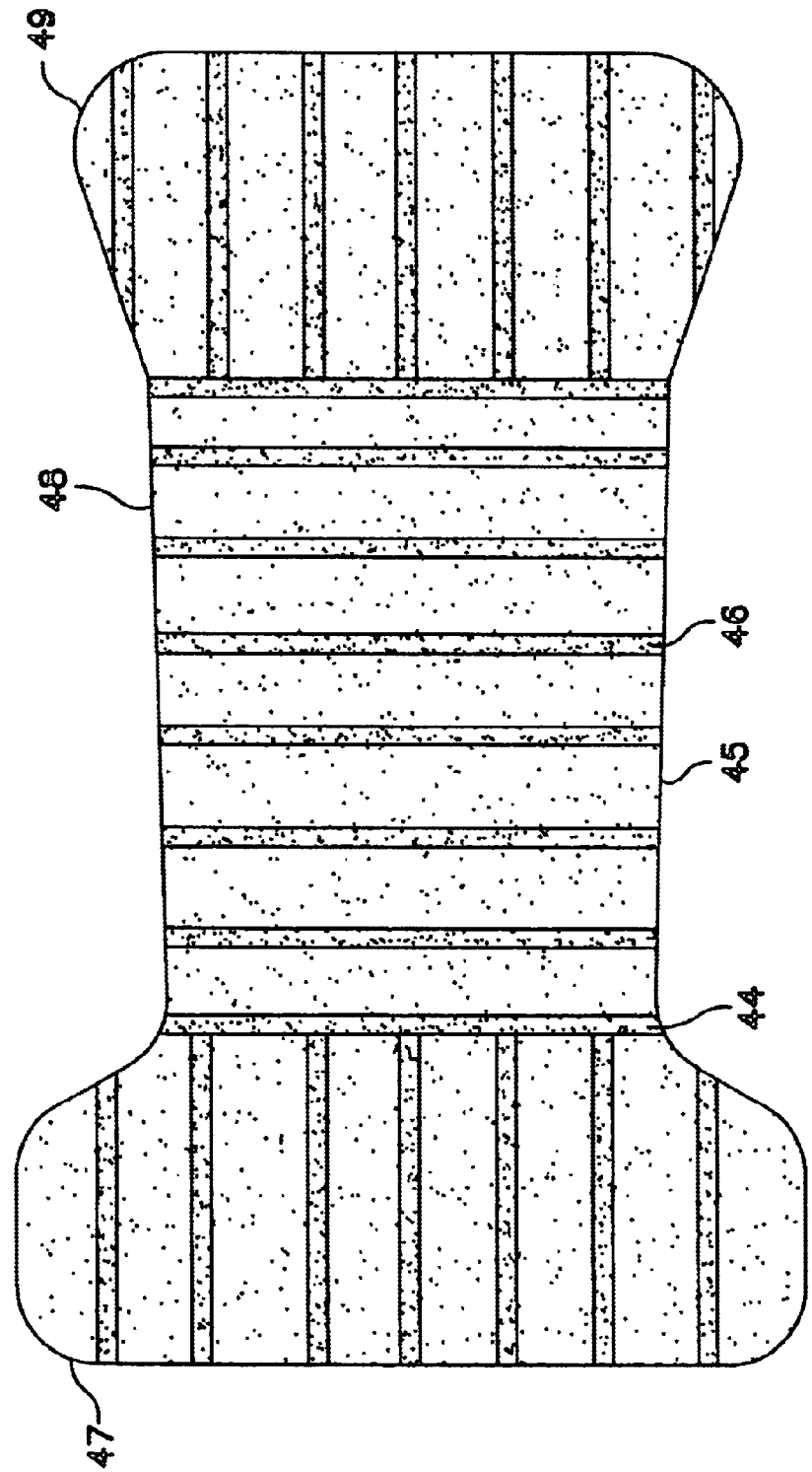
FIG. 2 is a plan view of an elastic absorbent nonwoven web composite useful in the absorbent article of the invention.

Referring to FIGS. 1 and 2, the absorbent composite 44 includes a plurality of relatively open, undensified regions 45, separated by bond lines representing densified regions 46. Absorbent composite 44 may include a central portion 48, which is stretchable in a first (longitudinal) direction 1, and two end portions 47 and 49, which are stretchable in a second (lateral) direction 2. These directions of preferred stretching are ideal for a diaper or pant-like absorbent garment, which preferably stretch longitudinally in the crotch region and laterally in the two waist regions. The portions 47, 48 and 49 may be provided using three pieces of an elastic absorbent nonwoven web composite, for instance, a coform composite as described above. Central portion 48 may be oriented so that its machine direction corresponds to the longitudinal direction 1. End portions 47 and 49 may be oriented so that their machine direction corresponds to the lateral direction 2. The portions 47, 48 and 49 may be joined at their respective edges using thermal bonding, ultrasonic bonding, adhesive bonding, mechanical stitch bonding, or the like.

The bond lines 46 in central portion 48 are oriented in the lateral direction 2, which is transverse to the direction of stretch in the central region. Bond lines 46 may somewhat reduce the longitudinal stretchability of the central portion 48, but may substantially eliminate any stretchability in the lateral direction. Additionally, bond lines 46 improve the strength of the composite 44 during stretching, and improve its elastic recovery, by reducing tearing of the elastic matrix filaments. Also, bond lines 46 reduce lateral separation of the matrix filaments, thereby reducing shake-out of the absorbent and superabsorbent during stretching and retraction.

The bond lines 46 in the end portions 47 and 49 are oriented in the longitudinal direction 1, which is transverse to the direction of stretch in end portions 47 and 49. Bond lines 46 may somewhat reduce the lateral stretchability of end portions 47 and 49, but may substantially eliminate any stretchability in the longitudinal direction. Again, the bond lines improve the strength and elastic recovery of the composite, and reduce shake-out of the absorbent and superabsorbent materials.

The bond lines 46 can be formed using heat bonding (e.g., a thermal calender bonding process), ultrasonic bonding, adhesive bonding, mechanical compression, or the like. Preferably, bond lines 46 cause compaction and densification of the absorbent composite in the bonded regions, so as to anchor the elastic matrix filaments in these regions. Desirably, the density of the absorbent composite in the bonded regions 46 may be about 1.5–3 times the density in the unbonded regions. The bond lines 46 should each have a thickness, or width in the direction of stretch (the machine direction) of about 0.5 mm to about 25 mm, suitably about 1 mm to about 15 mm, ideally about 2 mm to about 10 mm. The bond lines 46 should have a length, transverse to the direction of stretch, which is at least about 5 times their width, suitably at least about 10 times their width, desirably at least about 15 times their width. The bond lines 46 may be substantially continuous in length, or may be divided into closely spaced segments.

The bond lines should be thick enough, or wide enough, to cover a minor yet significant portion of the machine direction (direction of stretch) length of the absorbent composite. Referring to FIG. 2, for instance, the ratio of the thickness of bond lines 46 to the shortest distance between consecutive bond lines 46 should be at least about 1:20, suitably at least about 1:15, desirably at least about 1:10. At the same time, the bond lines 46 should not be so thick as to substantially impair the elasticity of the absorbent composite in the direction of stretch. To this end, the ratio of the thickness of bond lines 46 to the shortest distance between adjacent bond lines should be not more than about 1:1, suitably not more than about 1:3, desirably not more than about 1:5.

The bond lines 46 are preferably perpendicular to the direction of desired stretch, which is typically the machine direction. However, to have the desired effect, bond lines 46 may form angles anywhere between about 45–135 degrees relative to the direction of stretch. Suitably, bond lines 46 form angles between about 60–120 degrees, desirably between about 75–105 degrees, relative to the machine direction of stretch.

In order for the diaper 10 to have elasticity similar to absorbent composite 44 the other layers must be at least as stretchable, and may or may not be independently recoverable. Both the surge layer 42 and the body side liner 14 are constructed from highly liquid pervious materials. These layers function to transfer liquid from the wearer to the absorbent composite 44. Suitable materials include porous woven materials, porous nonwoven materials, and apertured films. Examples include, without limitation, any stretchable porous sheets of polymeric fibers, bonded carded webs of synthetic or natural fibers or combinations thereof. Either layer may also be an apertured stretchable plastic film.

The outer cover 12 may include a single stretchable layer, or may include multiple stretchable layers joined together by adhesive bonding, thermal bonding, ultrasonic bonding or the like. Outer cover 12 can be made from a wide variety of woven or nonwoven materials, films, or a film-coated nonwoven material, including, for instance, cast or blown films. Outer cover 12 may also be a composite of a bonded carded or spunbonded or meltblown material, for example, a spunbonded-meltblown composite of thermoplastic material or a spunbonded-meltblown-spunbonded thermoplastic material, wherein the spunbonded layer can provide a cloth-like texture and the meltblown layer can provide liquid impermeability. Outer cover 12 is preferably highly breathable to water vapor.

EXAMPLES

Absorbent composite coform samples were prepared using a process similar to the one described in U.S. Pat. No. 4,100,324, issued to Anderson et al. The samples had a basis weight of about 350–400 grams per square meter ("gsm") and a density of about 0.1 grams/cc. Each absorbent composite coform contained about 10% by weight substantially continuous meltblown fibers made from KRATON® G2740 elastomer from the Shell Chemical Co., about 40% by weight FAVOR®880 particulate superabsorbent from Stockhausen, and about 50% by weight cellulose fluff.

Rectangular test samples were cut measuring 30.5 cm in the machine direction, and 5.1 cm in the cross-machine direction. Some of the test samples were bonded at intervals using a Bransonic ultrasonic bonding apparatus with a rectangular anvil oriented perpendicular to the machine direction, so that the bonded regions were a preselected width in the machine direction, and 5.1 cm long in the cross-machine direction. The rectangular anvil was designed to impart about 10 closely-spaced point bonds per square centimeter, arranged in a pattern corresponding to the rectangle.

For Example 1, a control, no bond lines were imparted to the samples. For Example 2, ultrasonic bond lines having a 2 mm width, and separated by 17 mm of unbonded region, were imparted to the samples. For Example 3, ultrasonic bond lines having a 5 mm width, and separated by 40 mm of unbonded region, were imparted to the samples. The bonding approximately doubled the sample density in the bonded regions.

The test strips (about 5 per example) were then elongated using an Instron Model 5277 test apparatus, and the manufacturer's elongation procedure EMT029. For Example 1, the test strips were elongated to 200% of their initial length (doubled in length), resulting in significant separation and delamination of the elastomeric filament matrix from the cellulose fluff and superabsorbent. When allowed to retract, the test strips increased in thickness due to wrinkling of the separated cellulose fluff and superabsorbent, and did not completely recover to their initial length.

For Examples 2 and 3, the test strips were elongated to 200% of their initial length without any noticeable separation of the ingredients. In essence, the densified bond regions prevented overall separation of the ingredients. The loads required to stretch these samples were somewhat higher than for Example 1, due to the densified bond regions. Yet when allowed to retract, the test strips recovered substantially to their initial length.

While the embodiments of the invention disclosed herein are presently considered preferred, various modifications and improvements can be made without departing from the spirit and scope of the invention. The scope of the invention is indicated by the appended claims, and all changes that fall within the meaning and range of equivalency are intended to be embraced therein.

I claim:

1. An absorbent elastic nonwoven coform composite material, comprising:

an elastic filament matrix including a plurality of elastomeric nonwoven filaments; and contained within the matrix, absorbent fibers and a superabsorbent material;

the coform composite material having a machine direction corresponding to a primary direction of orientation of the elastomeric nonwoven filaments, and a plurality of undensified regions separated by bond lines oriented at angles in a range from about 60 degrees to about 120 degrees relative to the machine direction, the bond lines having a width of about 2 mm to about 25 mm, a length greater than the width, and a distance between adjacent bond lines greater than the width;

wherein the coform composite material has a density in the bond lines which is about 1.5–3 times a density in the undensified regions; and wherein the bond lines cause compaction and densification of the coform composite material, and the bond lines prevent separation of the elastic nonwoven filaments, the absorbent fibers and the superabsorbent material during stretching and improve elastic recovery of the elastic nonwoven coform composite.

2. The composite material of claim 1, comprising about 3 to less than 20% of the elastic filament matrix, about 20–77% by weight of the absorbent fibers, and about 20–77% by weight of the superabsorbent material.

3. The composite material of claim 1, comprising about 5–18% by weight of the elastic filament matrix, about 25–70% by weight of the absorbent fibers, and about 25–70% by weight of the superabsorbent material.

4. The composite material of claim 1, comprising about 5–15% by weight of the elastic filament matrix, about 30–62% by weight of the absorbent fibers, and about 40–65% by weight of the superabsorbent material.

5. The composite material of claim 1, wherein the bond lines each have a width of about 1–15 mm.

6. The composite material of claim 1, wherein the bond lines each have a width of about 2–10 mm.

7. The composite material of claim 1, wherein the bond lines each have a length which is at least about 5 times the width.

8. The composite material of claim 1, wherein the bond lines each have a length which is at least about 10 times the width.

9. An absorbent article comprising the composite material of claim 1.

10. The absorbent article of claim 9, comprising a diaper.

11. The absorbent article of claim 9, comprising training pants.

12. The absorbent article of claim 9, comprising swim wear.

13. The absorbent article of claim 9, comprising underpants.

14. The absorbent article of claim 9, comprising an adult incontinence product.

15. The absorbent article of claim 9, comprising a feminine hygiene product.

16. The absorbent article of claim 9, comprising a medical absorbent product.

17. An absorbent elastic nonwoven coform composite material, comprising:

an elastic filament matrix including a plurality of thermoplastic elastomeric nonwoven filaments; and contained within the matrix, absorbent fibers and a superabsorbent material;

the coform composite material having a central portion and two end portions;

each of the central and end portions having a machine direction corresponding to a primary direction of orientation of the thermoplastic elastomeric nonwoven filaments, and a plurality of undensified regions separated by nonintersecting bond lines, the bond lines oriented at angles in a range from about 60 degrees to about 120 degrees relative to the machine direction and having a width of about 2 mm to about 25 mm, a length greater than the width, and a distance between adjacent bond lines greater than the width;

wherein the coform composite material has a density in the bond lines which is about 1.5–3 times a density in the undensified regions; and wherein the bond lines in the central region are substantially perpendicular to the bond lines in the two end regions, and the bond lines cause compaction and densification of the coform composite material, and the bond lines prevent separation of the elastomeric nonwoven filaments, the absorbent fibers and the superabsorbent material during stretching and improve elastic recovery of the absorbent elastic nonwoven coform composite.

18. A diaper comprising the composite material of claim 17.

19. Training pants comprising the composite material of claim 17.

20. Swim wear comprising the composite material of claim 17.

21. Underpants comprising the composite material of claim 17.

22. An adult incontinence product comprising the composite material of claim 17.

23. A feminine hygiene product comprising the composite material of claim 17.

24. A medical absorbent product comprising the composite material of claim 17.

25. An absorbent article, comprising:

a liquid-permeable body-side liner;

a substantially liquid-impermeable outer cover; and an absorbent elastic nonwoven coform composite material between the body-side liner and the outer cover;

the coform composite material comprising an elastic filament matrix including a plurality of thermoplastic nonwoven elastomeric filaments, absorbent fibers, and a superabsorbent material;

the coform composite material having a machine direction corresponding to a primary direction of orientation of the thermoplastic elastomeric nonwoven filaments, and a plurality of undensified regions separated by bond lines oriented at angles in a range from about 60 degres to about 120 degrees relative to the machine direction, the bond lines having a width of about 2 mm to about 25 mm, a length greater than the width, and a distance between adjacent bond lines greater than the width;

wherein the coform composite material has a density in the bond lines which is about 1.5–3 times a density in the undensified regions; and wherein the bond lines cause compaction and densification of the coform composite material, and the bond lines prevent separation of the elastomeric nonwoven filaments, the absorbent fibers and the superabsorbent material during stretching and improve elastic recovery of the absorbent elastic nonwoven coform composite.

26. An absorbent article, comprising:

a liquid-permeable bodyside liner;

an outer cover; and an absorbent elastic nonwoven composite material between the liner and outer cover, the composite material having a central region and two end regions;

the composite material including a plurality of thermoplastic nonwoven elastomeric filaments, absorbent fibers, and a superabsorbent material;

the central region having a machine direction corresponding to a primary direction of orientation of the thermoplastic elastomeric nonwoven filaments, and a plurality of spaced apart bond lines oriented about 75–105 degrees relative to the machine direction; and wherein the bond lines in the central region are devoid of intersecting bond lines in the central region.

27. The absorbent article of claim 26, wherein the bond lines are oriented substantially perpendicular to the machine direction.

28. The absorbent article of claim 27, wherein the bond lines are extended across a width of the central region.

29. The absorbent article of claim 28, further comprising a plurality of bonds in the two end regions which are substantially perpendicular to the bond lines in the central region.

30. The absorbent article of claim 26, wherein the bond lines extend across a width of the central region.

31. The absorbent article of claim 26, further comprising a plurality of spaced apart bond lines in the two end regions.

32. The absorbent article of claim 31, wherein the bond lines in the two end regions are substantially perpendicular to the bond lines in the central region.

* * * * *